(12) United States Patent
Kim

(10) Patent No.: US 9,699,972 B2
(45) Date of Patent: *Jul. 11, 2017

(54) **STRAIN OF *PLEUROTUS NEBRODENSIS***

(71) Applicant: You Song Kim, Seoul (KR)

(72) Inventor: You Song Kim, Seoul (KR)

( * ) Notice: Subject to any disclaimer, the term of this patent is extended or adjusted under 35 U.S.C. 154(b) by 427 days.

This patent is subject to a terminal disclaimer.

(21) Appl. No.: 14/279,910

(22) Filed: May 16, 2014

(65) Prior Publication Data

US 2014/0345003 A1 Nov. 20, 2014

(30) Foreign Application Priority Data

May 20, 2013 (KR) .................. 10-2013-0056176

(51) Int. Cl.
*A01G 1/04* (2006.01)
*A01H 15/00* (2006.01)
*C05D 1/00* (2006.01)

(52) U.S. Cl.
CPC .............. *A01G 1/04* (2013.01); *A01H 15/00* (2013.01); *C05D 1/00* (2013.01)

(58) Field of Classification Search
CPC ....................................................... A01G 1/04
See application file for complete search history.

(56) References Cited

U.S. PATENT DOCUMENTS 9,351,445 B2 * 5/2016 Kim .................... A01G 1/04

OTHER PUBLICATIONS

Alam et al 2009 Mycobiology 37(3) : 183-188.*
Liu et al 2016 Int. J. Agric. Biol., 18: 198-203.*

* cited by examiner

*Primary Examiner* — David H Kruse
(74) *Attorney, Agent, or Firm* — IPLA P.A.; James E. Bame

(57) ABSTRACT

A novel strain of *Pleurotus nebrodensis* (Daewang No. 1, Accession No.: KACC93181P) and a method for cultivating it are provided. The novel strain of *Pleurotus nebrodensis* is different from the existing *Pleurotus ferulae* in shape and physiological characteristic, has an extra after-ripening period, can be grown at a low temperature of 22 to 25° C. and a low water content (RH) of 60 to 65%, can be cultivated in slightly acid environment of pH 5.5 to 6.5, can utilize bottle cultivation, and has a good shape not to be easily damaged in packaging. Thus, the novel strain of *Pleurotus nebrodensis* according to the present invention have good commercial value, are more resistant to environmental change, and can be mass produced by automation system and used for creating high value-added business in the food and agriculture industry.

7 Claims, 3 Drawing Sheets

STRAIN OF *PLEUROTUS NEBRODENSIS*

CROSS REFERENCE

This application claims foreign priority under the Paris Convention to Korean Patent Application No. 10-2013-0056176, filed 20 May 2013, which is hereby incorporated by reference in its entirety.

BACKGROUND OF THE INVENTION

1. Field of the Invention

The present invention relates to a novel strain of *Pleurotus nebrodensis* (Daewang No. 1, Accession No.: KACC93181P).

2. Description of the Related Art

Oyster mushroom (*Pleurotus* sp.) belongs to pine mushroom family, and is called "Chunhwasim" or "Mani" in Sino-Korean word. The oyster mushroom is often found all over Korea in autumn, in a dried main stem, a fallen stem, a hewn root and so on of broadleaf trees, such as oak, alder, cottonwood and willow trees. It is known that the oyster mushroom is spread in places like China, Japan, Europe, North America and Siberia as well as Korea. The fruit body of the oyster mushroom is sprouted about October to December and March to April, and the pileus of the oyster mushroom has a color of light-gray or gray-brown and a shape of semicircular or fanwise. It is desired that the pileus of the oyster mushroom has a diameter of 2 to 3 cm, and as it grows too big, the market value is depreciated. A log-cultivation method or a bottle-cultivation method using sawdust is used for the artificial cultivation of the oyster mushroom. The oyster mushroom is very low in calories and rich in cellulose and moisture, and gives the feeling of fullness.

*Pleurotus ferulae* is a grassland type saprophyte that prefers steppe climate. It has been known as *Pleurotus ferulae* because of being found around *Ferulae* tree in Xinjiang Province, China which is an arid region. Taxonomically, because *Pleurotus ferulae* is a controversial strain, it is classified in more than one species, as a variant species of King oyster mushroom (*Pleurotus eryngii* var. *ferulae*); or an independent species in the *Pleurotus* genus of the Pleurototaceae family of basidiomycetes (*Pleurotus ferulae*).

It is known that *Pleurotus ferulae* grows naturally in subtropical areas or grassland areas of Southern Europe, Czechoslovakia, Hungary, France, North Africa, Central Asia, South Russia and North America. In Japan *Pleurotus ferulae* is called "Baeng-Nyeong-Gi" or "Seor-Hal", and in China it is called "A-Wie-Chuk-Yi", "A-Wie-Go" or "Baeng-Nyeong-Go". Further, because *Pleurotus ferulae* is shaped similar to "Baeng-Nyeong" oyster mushroom (*Pleurotus nebrodensis*), they are named to be mixed.

*Pleurotus ferulae* is a little breed of mushroom produced about 1,000 ton per a year worldwide. Compared to other mushrooms, *Pleurotus ferulae* has a good figure, a full flavor, a high edibility value, and is effective in anti-aging, anti-tumor, anemia alleviation, blood pressure regulation and blood sugar reduction. Further, it is known that *Pleurotus ferulae* can improve stomach and kidney functions, keep under a cough and remove inflammation, and be useful in obstetrics and gynecology diseases. *Pleurotus ferulae* has a lot of dietary fiber, amino acids and vitamin, and is well worth a health functional food and a functional medicated mushroom. Recently, in Japan, *Pleurotus ferulae* is being used for food because of very valuable as food and medicine, and thereby increasing its demand continuously.

However, although *Pleurotus ferulae* is very valuable as food and medicine, it has been providing and circulating only in small quantity to actual consumers. The annual production of *Pleurotus ferulae* is small and the produced mushrooms are easily damaged in harvesting and packaging. Therefore, it is difficult to provide high quality of *Pleurotus ferulae* that consumers want.

Thus, various studies are being carried out briskly to provide high quality of *Pleurotus ferulae* for consumers, and patent applications about this are being increased. Registered Korean Patent No. 10-0403411 (Oct. 15, 2003) discloses "The NOVEL *PLEUROTUS FERULAE*-K9 AND THE CULTURE METHOD FOR THEREOF", but it takes long period of 82 days from inoculation of the strain of *Pleurotus ferulae* in a medium to germinating of mushroom. Although being grown during the long cultivation period, many mushrooms have a fat body and are produced with deformed stipe and pileus. Thus, the quality of products is considerably degraded and not available on the market.

On the other hand, in case of an introduced species whose production and sale were reported in Korean Seed Management Office in 2007, the mushroom was introduced from China in 2003 and bottle cultivation was being attempted. However, the fruit body of the mushroom is obese and the pileus is a funnel shaped oblate structure about ½ length of stripe, so that the shape of the mushroom and its fruit body is not suitable for the bottle cultivation. Therefore, the species introduced from China is not also available on the market.

Most of *Pleurotus ferulae* patent-applied and improved until now have very low merchantable quality or its shape is not suitable. Thus, the bottle cultivation is impossible and therefore mass production is impossible. Therefore, the supply and distribution for actual consumers are not being carried out. Further, in order to mass produce and provide to consumers, we should develops a new variety of *Pleurotus ferulae* should be developed and a new medium and a cultivation method are provided, which have little restrictions on climate, time and space, and can be produced automatically by machines.

SUMMARY OF THE INVENTION

In order to solve the above problems and to be capable of providing *Pleurotus ferulae* for consumers, the present inventors researched *Pleurotus ferulae* which has high quality and can be mass produced, and as a result, found a novel strain of *Pleurotus nebrodensis* different from the existing *Pleurotus ferulae* in shape and physiological characteristic. The novel strain of *Pleurotus nebrodensis* according to the present invention has an extra after-ripening period, can be grown at a low temperature of 22 to 25° C. and a low water content (RH) of 60 to 650, can be cultivated in slightly acid environment (pH 5.5 to 6.5), can utilize bottle cultivation, and has a good shape not to be easily damaged in packaging. Thus, the novel strain of *Pleurotus nebrodensis* according to the present invention have good commercial value, are more resistant to environmental change, and can be mass produced by automation system.

It is an object of the present invention to provide a novel strain of *Pleurotus nebrodensis* (Daewang No. 1, Accession No.: KACC93181P).

It is another object of the present invention to provide a medium of the novel strain of *Pleurotus nebrodensis*.

It is still another object of the present invention to provide a cultivation method of the novel strain of *Pleurotus nebrodensis*.

It is yet another object of the present invention to provide a fruit body formed from the novel strain of *Pleurotus nebrodensis*.

The present invention provides a novel strain of *Pleurotus nebrodensis* (Daewang No. 1, Accession No.: KACC93181P).

Further, the present invention provides a medium of the novel strain of *Pleurotus nebrodensis*.

The present invention provides a cultivation method of the novel strain of *Pleurotus nebrodensis*.

The present invention provides a fruit body formed from the novel strain of *Pleurotus nebrodensis*.

The novel strain of *Pleurotus nebrodensis* according to the present invention is different from the existing *Pleurotus ferulae* in shape and physiological characteristic. The novel strain of *Pleurotus nebrodensis* according to the present invention has an extra after-ripening period, can be grown at a low temperature of 22 to 25° C. and a low water content (RH) of 60 to 650, can be cultivated in slightly acid environment of pH 5.5 to 6.5, can utilize bottle cultivation, and has a good shape not to be easily damaged in packaging. Thus, the novel strain of *Pleurotus nebrodensis* according to the present invention have good commercial value, are more resistant to environmental change, and can be mass produced by automation system. In conclusion, the present invention could be used for creating high value-added business in the food and agriculture industry.

DETAILED DESCRIPTION OF THE INVENTION

Figure 1:
FIGS. 1 to 6 show cultivation pictures of a novel strain of *Pleurotus nebrodensis* according to the present invention.
Figure 2:
Figure 3:
Figure 4:
Figure 5:
Figure 6:

The present invention provides a novel strain of *Pleurotus nebrodensis*, which is designated Daewang No. 1, representative having been deposited at the Korean Agricultural Culture under Accession Number KACC93181P.

Further, the present invention provides a medium of the novel strain of *Pleurotus nebrodensis*.

The present invention will now be described in detail.

The novel strain of *Pleurotus nebrodensis* according to the present invention is characterized as being obtained by the following steps: isolating each of mono-spores from selected fruit bodies of *Pleurotus ferulae* and examining the toxicity of mononuclear strain; manufacturing mono-spore hybrid strains between each of strains; and selecting good quality of strains by cultivation and productivity examination.

*Pleurotus ferulae* used in the present invention can be obtained by gathering or purchasing.

In the present invention, the novel strain of *Pleurotus nebrodensis* can be obtained by the below described method.

Original strains are obtained from fruit bodies of *Pleurotus ferulae* firstly gathered, and stabilization of medium is carried out with the productivity examination. *Pleurotus ferulae* secondly gathered is incubated in the stabilized medium, and the productivity examination is carried out. The most stable strains of them are selected. Mono-spores are isolated from fruit bodies formed by the selected strains and the feature of mononuclear strain is examined. And mono-spore hybrid strains between each of strains are manufactured and it is identified whether the manufactured mono-spore hybrid strains are hybridized. The hybridized strains are selected, artificially cultivated several times, and the productivity examination is carried out. And then by selecting the best one species of strains, the novel strain of *Pleurotus nebrodensis* according to the present invention can be obtained, which is excellent in productivity and stability.

It is desirable that the medium comprises cotton seed husk of 30 to 50 vol %, corn powder of 2 to 8 vol %, wheat bran of 5 to 15 vol %, rice bran of 2 to 8 vol %, cotton seed meal of 2 to 8 vol %, corn cob of 10 to 26 vol %, sugar cane of 5 to 15 vol %, tangerine peel powder of 0.2 to 0.8 vol %, sugar of 0.2 to 0.8 vol %, soybean cake of 2 to 8 vol % and gypsum of 0.5 to 1.5 vol % (v/v %) based on total volume of the medium, but is not limited thereto.

It is desirable to maintain the water content (RH) of the medium at 65%, but not limited thereto. Further, it is desirable to maintain the pH of the medium at 5.5 to 6.5, but is not limited thereto.

It is desirable to incubate *Pleurotus nebrodensis* in the medium, but is not limited thereto.

It is desirable that bottle cultivation is used to cultivate *Pleurotus nebrodensis*, but is not limited thereto.

It is desirable that the optimum growth temperature of the strain of *Pleurotus nebrodensis* is 22 to 25° C., but is not limited thereto.

It is desirable that the optimum growth humidity (RH) of strain of *Pleurotus nebrodensis* is 60 to 65%, but is not limited thereto.

It is desirable that the optimum growth acidity (pH) of strain of *Pleurotus nebrodensis* is 5.5 to 6.5, but is not limited thereto.

It is desirable that after-ripening period is included in cultivation process of *Pleurotus nebrodensis*, but is not limited thereto.

The novel strain of *Pleurotus nebrodensis* according to the present invention is different from the existing *Pleurotus ferulae* in shape and physiological characteristic, has an extra after-ripening period, can be grown at a low temperature of 22 to 25° C. and a low water content (RH) of 60 to 650, can be cultivated in slightly acid environment of pH 5.5 to 6.5, can utilize bottle cultivation, and has a good shape not to be easily damaged in packaging. Thus, the novel strain of *Pleurotus nebrodensis* according to the present invention have good commercial value, are more resistant to environmental change, and can be mass produced by automation system. In conclusion, the present invention could be used for creating high value-added business in the food and agriculture industry.

The present invention provides a method for cultivating a novel strain of *Pleurotus nebrodensis*.

It is desirable that the cultivating method comprises the steps as follows:

1) manufacturing a medium comprising cotton seed husk of 30 to 50 vol %, corn powder of 2 to 8 vol %, wheat bran of 5 to 15 vol %, rice bran of 2 to 8 vol %, cotton seed meal of 2 to 8 Vol %, corn cob of 10 to 26 vol %, sugar cane of 5 to 15 vol %, tangerine peel powder of 0.2 to 0.8 vol %, sugar of 0.2 to 0.8 vol %, soybean cake of 2 to 8 vol % and gypsum of 0.5 to 1.5 vol % based on total volume of the medium;

2) putting the medium in bottles and sterilizing by high pressure;

3) inoculating the sterilized medium with seed of *Pleurotus nebrodensis* and incubating the seed;

4) thinning out a part of *Pleurotus nebrodensis* produced in the incubated medium, and incubating the rest during an after-ripening period; and 5) growing up the incubated *Pleurotus nebrodensis*.

The cultivating method is not limited to the above described steps but may include alternative or additional steps if necessary.

The cultivating method of the novel strain of *Pleurotus nebrodensis* can be industrialized and bottle-cultivated. Further, because little manpower and small space are required for the method, it can be cultivated by automation system and mass produced.

The present invention also provides a fruit body of the novel strain of *Pleurotus nebrodensis*.

Exemplary embodiments of the present invention will now be described for understanding of the present invention. The following embodiments provide for understanding of the present invention and are not intended to limit a technical scope of the present invention.

Embodiment 1: Manufacturing of a Novel Strain of *Pleurotus nebrodensis*

In order to manufacture the novel strain of *Pleurotus nebrodensis* according to the present invention, we have visited Xinjiang Province, China, and firstly gathered wild *Pleurotus ferulae*. After returning to Korea, we obtained original strain from the fruit body of the gathered *Pleurotus ferulae*, and tried to cultivate the obtained original strain artificially.

The original strain is incubated in a medium which comprises cotton seed husk of 30 to 50 vol %, corn powder of 2 to 8 vol %, wheat bran of 5 to 15 vol %, rice bran of 2 to 8 vol %, cotton seed meal of 2 to 8 vol %, corn cob of 10 to 26 vol %, sugar cane of 5 to 15 vol %, tangerine peel powder of 0.2 to 0.8 vol %, sugar of 0.2 to 0.8 vol %, soybean cake of 2 to 8 vol % and gypsum of 0.5 to 1.5 vol % based on total volume of the medium. And the stabilization of the medium was carried out with repetitive productivity examination.

In order to breed a strain different from the existing species, *Pleurotus ferulae* was gathered secondly, the gathered *Pleurotus ferulae* was incubated in the stabilized medium, and the productivity examination was carried out. Three strains were gathered, two of them stable for cultivating were selected, and mono-spores were isolated from fruit bodies formed by the selected two strains, respectively.

Using the isolated mono-spores, the feature of mononuclear strain was examined, and total 100 mono-spore hybrid strains between each of strains were manufactured. The clamp connection of the manufactured mono-spore hybrid strains was observed with a microscope to identify whether the manufactured mono-spore hybrid strains are hybridized. The mono-spore hybridization was tried for total 100 strains, 73 strains of them, in which hybridization was identified, were selected. The selected 73 strains were cultivated several times by a bag cultivation method, and the productivity examination was carried out. And then best strains were selected by investigating shape of pileus, color and gloss of pileus, thickness of stipe, length of stipe and so on of the fruit body grown in the cultivation test. The selected strains have a short duration of incubation and cultivation, are large in number, have an umbrella shaped pileus, and have a fleshy body dense rather than hard. The productivity examination was carried out for selected 73 strains from the mono-spore hybridization described in the above, and the best one strain was selected. As a result, a novel strain designated Daewang No. 1 is a selected interspecific hybrid between *Pleurotus ferulae* and *Pleurotus nerbrodensis*.

The present inventors confirmed the obtained novel strain as a novel strain of *Pleurotus nebrodensis* according to the present invention, and deposited it to the RDA-Genebank Information Center of the Korean Academy of Agricultural Science on Apr. 22, 2013 (Accession name: Daewang No. 1, Accession No.: KACC93181P)

Embodiment 2: Cultivation Conditions of a Novel Strain of *Pleurotus nebrodensis*

(a) Manufacturing of Medium

A medium of a novel strain of *Pleurotus nebrodensis* was manufactured, which comprises cotton seed husk of 40 vol %, corn powder of 5 vol %, wheat bran of 10 vol %, rice bran of 5 vol %, cotton seed meal of 5 vol %, corn cob of 18 vol %, sugar cane of 10 vol %, tangerine peel powder of 0.5 vol %, sugar of 0.5 vol %, soybean cake of 5 vol % and gypsum of 1 vol % based on total volume of the medium.

The water content (RH) of the medium was maintained at 65%, and the pH was maintained at 5.5 to 6.5.

(b) Preparing of Incubation Container

Incubation containers of 1100 cc×75, 1300 cc×80 and 1400 cc×85 were prepared for bottle cultivation.

(c) Sterilizing of Medium and Incubation Container

The medium manufactured in (a) were put in the containers prepared in (b). And then the containers filled with the medium were high-pressure sterilized at 105° C. and 0.2 kgf/cm² for 3 hours, and cooled at room temperature.

(d) Incubating Condition

The medium cooled in (c) was inoculated at 22 to 25° C. in the darkroom for 25 days, and an after-ripening process was carried out at 18 to 21° C. for 20 day.

(e) Growth Condition of Fruit Body

The fruit bodies formed in (d) were grown up under the condition of a temperature of 13 to 15° C., a relative humidity (RH) of 85 to 95% and a density of carbon dioxide of below 1,000 ppm, for 20 to 25 days.

Comparative Example: Obtaining and Cultivation Condition of *Pleurotus ferulae*

1. Obtaining of *Pleurotus ferulae*

*Pleurotus ferulae* (or "A-Wie-Go") firstly gathered in Embodiment 1 was used as a comparison group. The *Pleurotus ferulae* not bred or hybridized was used as it is, without further processing.

2. Cultivation Conditions of *Pleurotus ferulae*

(a) Manufacturing of Medium (1) Medium A

Medium A of *Pleurotus ferulae* was manufactured, which comprises sawdust of 24.09 vol %, wheat bran of 6.02 vol %, cotton seed meal of 6.02 vol %, corn cob of 9.03 vol %, rice bran of 3.01 vol %, soybean cake of 3.01 vol %, sugar cane of 7.83 vol %, tangerine peel powder of 0.6 vol %, lime hydrate of 0.6 vol %, red candy ("Hong tang") of 0.6 vol % and water of 65.0 vol % (v/v %) based on total volume of the medium.

(2) Medium B

Medium B of *Pleurotus ferulae* was manufactured, which comprises cotton seed husk of 30.0 vol %, cotton seed meal of 6.06 vol %, wheat bran of 7.27 vol %, sugar of 0.6 vol %, soybean cake of 3.03 vol %, corn cob of 12.12 vol %, lime of 0.6 vol %, tangerine peel powder of 0.6 vol % and water of 39.39 vol % (v/v %) based on total volume of the medium.

(3) Water Content and Acidity Control

The water content (RH) of mediums A and B manufactured in (1) and (2) was maintained at 60 to 70%, and the pH was maintained at 7.5 to 8.5.

(b) Preparing of Incubation Container

Incubation containers of 1100 cc×75, 1300 cc×80 and 1400 cc×85 were prepared for bottle cultivation.

(c) Sterilizing of Medium and Incubation Container

The medium A and B manufactured in (a) were put in the containers prepared in (b). And then the containers filled with the medium were high-pressure sterilized at 105° C. and 0.2 kgf/cm$^2$ for 3 to 4 hours, and cooled at room temperature.

(d) Incubating Condition

The medium cooled in (c) was incubated at 22 to 25° C. in the darkroom for 25 to 30 days.

(e) Growth Condition of Fruit Body

The fruit bodies formed in (d) were grown up under condition of a temperature of 13 to 18° C., a relative humidity (RH) of 85 to 95% and a density of carbon dioxide below 1,000 ppm, for 20 to 25 days.

Embodiment 3: Incubating and Cultivating of a Novel Strain of Pleurotus nebrodensis In order to incubate and cultivate a novel strain of Pleurotus nebrodensis according to the present invention, the following described processes were carried out.

In order to manufacture the medium of the novel strain of Pleurotus nebrodensis described in (a) of Embodiment 2, all base materials of the medium described above were mixed by a mixer (SG-4600D) for 40 minutes. Underground water was added to the mixture and mixed for 60 to 90 minutes so that water content of the medium was adjusted at a humidity of 60 to 650, and then the medium was put in bottles. The bottles filled with the medium was sterilized at high temperature (by a dry sterilizer 14-LMC or a high pressure sterilizer SHW-M110), and then cooled. The seed cut off oxygen by sealing the bottles was parceled out to a growth chamber, and laid and stacked on the frames installed in the growth chamber. It is desirable that the bottles are stacked up in three stages and the frames are installed in four or five stages. After adopting the seed, the growth chamber was maintained at a temperature of 15 to 18° C. and was observed for 7 to 10 days without opening the bottles. After adopting, the growth chamber was not humidified, the density of carbon dioxide of the chamber was maintained below 1,000 ppm, and light of 1000 to 1500 lux was supplied to the chamber for 10 to 12 hours per day. Hyphae have formed again, and the mushroom has begun to germinate. When fruit bodies of the mushroom in the bottles were grown up to the size of a soybean, the bottles are opened. After opening the bottles, when mushrooms were grown up to the size of a corn ear, only one mushroom grown up to the fullest was reserved, but the rest were thinned out. And then, for after-ripening, in the growth chamber, the humidity was maintained at 85 to 900, the temperature was maintained at 13 to 15° C. (by using a constant-temperature oven C-1B2, 3, 4), a density of carbon dioxide was adjusted below 700 ppm, and light of 1000 to 1500 lux was supplied for 10 to 12 hours per day. The mushrooms were harvested on 10th to 12th day from germination, and the growth chamber was not humidified on 1 day before harvest time. Of the obtained mushrooms, the mushrooms of 150 to 170 g had highest quality.

Embodiment 4: Comparison of Shape Characteristics Between a Novel Strain of Pleurotus nebrodensis and of Pleurotus ferulae In order to compare shape characteristics between the novel strain of Pleurotus nebrodensis according to the present invention and Pleurotus ferulae of the comparison group, the shape analysis was carried out for the novel strain of Pleurotus nebrodensis manufactured in Embodiment 1, Pleurotus ferulae prepared in Comparative Example and the fruit bodies of Pleurotus nebrodensis obtained Embodiment 3.

1. Pileus

The pileus of the novel strain of Pleurotus nebrodensis had high white color similar to the comparison group. Further, the pileus had globular shape and its length was measured to be 10 to 15 cm. On the other hand, the pileus of Pleurotus ferulae of the comparison group had semispherical shape and its length was measured to be 6 to 13 cm.

2. Stipe

The stipe of the novel strain of Pleurotus nebrodensis was thick and short comparatively, and its length is measured to be 2 to 3 cm. Further, the width of the stipe of the novel strain of Pleurotus nebrodensis was measured to be 2 to 3 cm so that the ratio of length to width is identified to be 1:1.

On the other hand, the stipe of Pleurotus ferulae of the comparison group was thick and long, and its length is measured to be 3 to 8 cm. Further, the width of the stipe of Pleurotus ferulae was measured to be 4 to 6 cm so that the ratio of length to width is identified to be 3:1.

3. Fruit Body

The novel strain of Pleurotus nebrodensis has a structure in which fruit body includes the stipe, and the shape of the fruit body is globular. Further, the fruit body of the novel strain of Pleurotus nebrodensis was ontogeny type the same as that of Pleurotus ferulae of the comparison group, but its shape was more stable relatively.

Embodiment 5: Comparison of Physiological Characteristics Between a Novel Strain of Pleurotus nebrodensis and of Pleurotus ferulae In order to compare physiological characteristics between the novel strain of Pleurotus nebrodensis according to the present invention and Pleurotus ferulae of the comparison group, optimum temperature, optimum water content and optimum acidity of strain growth were compared between the novel strain of Pleurotus nebrodensis manufactured in Embodiment 1 and Pleurotus ferulae prepared in Comparative Example.

1. Optimum Temperature of Strain Growth

It was identified that the optimum temperature of strain growth of the novel strain of Pleurotus nebrodensis is 22 to 25° C., and the optimum temperature in the after-ripening period is 18 to 21° C. On the other hand, it was identified that the optimum temperature of strain growth of Pleurotus ferulae is 25 to 28° C., and there are not an extra after-ripening period, unlike the novel strain of Pleurotus nebrodensis according to the present invention.

Therefore, it was identified that the novel strain of Pleurotus nebrodensis according to the present invention can be grown at lower temperature than Pleurotus ferulae of the comparison group and has an extra after-ripening period.

2. Optimum Water Content of Strain Growth

It was identified that the optimum water content (RH, %) of strain growth of the novel strain of *Pleurotus nebrodensis* is 60 to 650. On the other hand, it was identified that the optimum water content of strain growth of *Pleurotus ferulae* is 65 to 70%.

Therefore, it was identified that the novel strain of *Pleurotus nebrodensis* according to the present invention can be grown at lower water content than *Pleurotus ferulae* of the comparison group.

3. Optimum Acidity of Strain Growth

It was identified that the optimum acidity (pH) of strain growth of the novel strain of *Pleurotus nebrodensis* is pH 5.5 to 6.5. On the other hand, it was identified that the optimum acidity of strain growth of *Pleurotus ferulae* is pH 7.5 to 8.5.

Therefore, it was identified that the novel strain of *Pleurotus nebrodensis* according to the present invention can be grown in slightly acid condition.

While the invention has been shown and described with reference to a certain preferred embodiment thereof, it will be understood by those skilled in the art that various changes in form and details may be made therein without departing from the spirit and scope of the invention as defined by the appended claims.

[Accession Number]

Depositary authority: RDA-Genebank Information Center of the Korean Academy of Agricultural Science Accession No.: KACC93181P Accession Date: 20130422

What is claimed is:

1. A novel strain of *Pleurotus* nebrodensis designated Daewang No. 1, representative inoculum having been deposited at the Korean Agricultural Culture under Accession Number KACC93181P.

2. A method for incubating the novel strain of *Pleurotus* nebrodensis according to claim 1, the method comprising a step for incubating the *Pleurotus* nebrodensis in a medium comprising cotton seed husk of 30 to 50 vol %, corn powder of 2 to 8 vol %, wheat bran of 5 to 15 vol %, rice bran of 2 to 8 vol %, cotton seed meal of 2 to 8 vol %, corn cup of 10 to 26 vol %, sugar cane of 5 to 15 vol %, tangerine peel powder of 0.2 to 0.8 vol %, sugar of 0.2 to 0.8 vol %, soybean cake of 2 to 8 vol % and gypsum of 0.5 to 1.5 vol % (v/v %) based on total volume of the medium.

3. The method for incubating the novel strain of *Pleurotus* nebrodensis according to claim 2, wherein optimum temperature of strain growth is 22 to 25° C.

4. The method for incubating the novel strain of *Pleurotus* nebrodensis according to claim 2, wherein optimum humidity (RH) of strain growth is 60 to 65%.

5. The method for incubating the novel strain of *Pleurotus* nebrodensis according to claim 2, wherein optimum acidity (pH) of strain growth is 5.5 to 6.5.

6. The method for incubating the novel strain of *Pleurotus* nebrodensis according to claim 2, wherein after-ripening period is included in cultivation process.

7. The method for incubating the novel strain of *Pleurotus* nebrodensis according to claim 2, wherein the after-ripening period is processed at a temperature of 18 to 21° C.

* * * * *